United States Patent
Meyer et al.

(10) Patent No.: US 6,187,957 B1
(45) Date of Patent: Feb. 13, 2001

(54) PREPARATION OF AMINES

(75) Inventors: Gerald Meyer, Ludwigshafen; Frank Funke, Limburgerhof; Gerhard Schulz, Ludwigshafen; Detlef Kratz, Heidelberg; Marc Walter, Frankenthal; Michael Hesse, Worms, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/459,856

(22) Filed: Dec. 14, 1999

(30) Foreign Application Priority Data

Dec. 23, 1998 (DE) ................................. 198 59 776

(51) Int. Cl.$^7$ .................................................. C07C 209/00
(52) U.S. Cl. ...................... 564/473; 564/397; 564/401; 564/446; 564/447; 564/472; 564/479; 546/184; 546/246
(58) Field of Search ...................... 564/597, 401, 564/446, 447, 472, 473, 479; 546/184, 246

(56) References Cited

U.S. PATENT DOCUMENTS 4,772,750  9/1988  Habermann ......................... 564/472

FOREIGN PATENT DOCUMENTS

| 2758769 | 7/1979 | (DE) . |
| 195 07 007 | 8/1996 | (DE) . |
| 197 42 911 | 4/1999 | (DE) . |
| 315189 | 5/1989 | (EP) . |
| 320074 | 6/1989 | (EP) . |
| 07323226 | 12/1995 | (JP) . |
| 644526 | 1/1979 | (SU) . |
| 464178 | 2/1980 | (SU) . |
| 968029 | 10/1982 | (SU) . |
| 1113375 | 9/1984 | (SU) . |
| 96/38226 | 12/1996 | (WO) . |

*Primary Examiner*—Samuel Barts
(74) *Attorney, Agent, or Firm*—Keil & Weinkauf (57) ABSTRACT

Amines are prepared by reacting primary or secondary alcohols, aldehydes or ketones with nitrogen compounds selected from the group consisting of ammonia and primary and secondary amines at elevated temperatures and superatmospheric pressures in the presence of hydrogen and of a catalyst containing copper and oxygen-containing compounds of titanium by a process in which the catalyst is used in the form of moldings which have been prepared with the addition of metallic copper powder.

11 Claims, 2 Drawing Sheets

FIG.1

FIG.2

PREPARATION OF AMINES

The present invention relates to a process for the preparation of primary, secondary or tertiary amines by reacting primary or secondary alcohols, aldehydes or ketones with nitrogen compounds selected from the group consisting of ammonia and primary and secondary amines at elevated temperatures and superatmospheric pressures in the presence of hydrogen and of a catalyst containing copper and oxygen-containing compounds of titanium.

The preparation of amines by the catalytic amination of alcohols, aldehydes or ketones in the presence of hydrogen plays an important role in the chemical industry. The reaction products are used mainly as process chemicals (for example, blowing agents for polyurethane production), catalysts (for the preparation of surfactants and polymers) and intermediates for relatively highly finished products, for example dyes and crop protection agents.

SU-A-644 526 (Derwent Abstract no. 76773B/42) describes the alkylation of aromatic amines by reaction with alcohols in the gas phase at elevated temperatures in the presence of hydrogen and a catalyst consisting of 45% by weight of CuO, 19% by weight of $Cr_2O_3$, 25% by weight of $TiO_2$, 6% by weight of BaO and 5% by weight of graphite.

SU-A-464 178 (Derwent Abstract no. 49191C/28) discloses a synthesis for morpholine by reacting diethylene glycol with ammonia in the presence of hydrogen and a nickel-copper-chromium-titanium catalyst at from 200 to 250° C.

SU-A-968 029 (Derwent Abstract no. 83-746162/34) and SU-A-1 113 375 (Derwent Abstract no. 85-085786/14) describe the simultaneous preparation of 2-amino-2'-hydroxydiethyl ether and morpholine by reacting diethylene glycol with ammonia at from 180 to 230° C. in the presence of hydrogen and of a catalyst containing 24–36 mol % of Ni, 25–35 mol % of Cu, 1–7 mol % of $Cr_2O_3$ and 27–51 mol % of Ti.

DE-A-27 58 769 discloses a process for the preparation of morpholine by reacting diethylene glycol with ammonia in the presence of $H_2$ in the vapor phase and in the presence of a catalyst composed of from 25 to 55% by weight of NiO, from 15 to 40% by weight of CuO, from 0.7 to 7% by weight of $Cr_2O_3$ and from 20 to 40% by weight of $TiO_2$.

The disadvantage of these catalysts is that, owing to their chromium content, they present problems with regard to environmental pollution.

DE-A-19 50 7007 reports a process for the amination of alcohols in the presence of catalysts consisting of from 0.001 to 25% by weight of Ru and from 0 to 5% by weight of promoters, for example Pd, Cu and Cr, on porous oxides, such as $Al_2O_3$, $SiO_2$, $TiO_2$ or $ZrO_2$.

WO 96/38226 relates to rhenium catalysts containing nickel, cobalt, boron and copper and/or ruthenium on a support and their use for the hydrogenation of alcohols under aminating conditions.

JP-A-07 323 226 (Derwent Abstract no. 96-064983/07) relates to Ni-Al catalysts for the amination of aliphatic alcohols.

U.S. Pat. No. 4 772 750 describes, in examples 3 and 4, the amination of monoethanolamine with ammonia in the presence of $H_2$ and a Cu-Co-$TiO_2$ catalyst which was prepared by a special salt melt impregnation method.

EP-A-320 074 relates to supported Cu catalysts having an Fe promoter, the support being, for example, $SiO_2$, $TiO_2$ or $Al_2O_3$, and their use for, inter alia, hydrogenation of alcohols under aminating conditions.

EP-A-315 189 reports mixed oxide catalysts containing niobium oxide and titanium, aluminum, silicon and zirconium oxides and/or oxides of the elements of groups II A, V A, VI A, I B, II B, III B, V B, VI B, VII B or VIII of the Periodic Table and their use in the hydrogenation of alkanolamines under aminating conditions.

The prior German application no. 19809418.3 relates to a process for the catalytic hydrogenation of carbonyl compounds in the presence of a copper catalyst which contains $TiO_2$, the copper catalyst as such and a process for its preparation.

The prior German applications no. 19742911.4 and 19826396.1 relate to processes for the preparation of amines by reacting primary or secondary alcohols with nitrogen compounds selected from the group consisting of ammonia and primary and secondary amines at from 80 to 250° C. and from 0.1 to 40 MPa and with hydrogen in the presence of a catalyst containing zirconium, copper and nickel.

It is an object of the present invention to provide an improved economical process for the preparation of amines from primary or secondary alcohols, aldehydes or ketones, the catalyst used being technically easy to prepare, permitting high conversions and selectivities, i.e. high space-time yields of the product, and having high chemical and mechanical stability and activity and a long life under the reaction conditions occurring in said process.

We have found that this object is achieved by a process for the preparation of amines by reacting primary or secondary alcohols, aldehydes or ketones with nitrogen compounds selected from the group consisting of ammonia and primary and secondary amines at elevated temperatures and superatmospheric pressures in the presence of hydrogen and of a catalyst containing copper and oxygen-containing compounds of titanium, wherein the catalyst is used in the form of moldings which have been prepared with the addition of metallic copper powder.

The admixing of metallic Cu powder before the shaping of the catalyst material into moldings, for example pellets, it being possible also to add conventional molding assistants, such as graphite, to the dried and powdered catalyst material, which comprises catalytically active material and, if required, inert material, before the shaping, leads a) to shaping which is particularly easy to carry out, b) to high activities and selectivities in the novel process and c) to high chemical and mechanical stability of the catalyst molding both in the oxidic and in the reduced state.

The catalytically active material of the molded catalysts used in the novel process contains, after their final heat treatment and before their reduction with hydrogen, from 20 to 83, preferably from 25 to 75, particularly preferably from 30 to 68, % by weight, calculated as $TiO_2$, of oxygen-containing compounds of titanium, from 15 to 60, preferably from 20 to 55, particularly preferably from 22 to 50, % by weight, calculated as CuO, of oxygen-containing compounds of copper, and from 2 to 29, preferably from 5 to 25, particularly preferably from 10 to 22, % by weight of metallic copper, which was added before the shaping of the catalyst material.

A part, for example from 5 to 50, in particular from 30 to 50, % by weight of the oxygen-containing compounds of titanium (e.g. $TiO_2$) can be replaced by oxygen-containing compounds of aluminum, e.g. alumina ($Al_2O_3$), and/or oxygen-containing compounds of zirconium, such as zirconium dioxide ($ZrO_2$), and/or oxygen-containing compounds of silicon, e.g. silica ($SiO_2$).

The catalytically active material of the catalysts used in the novel process may furthermore contain one or more elements, or the inorganic or organic compounds thereof, selected from the groups I A, II A, III B, IV B, V B, VI B, VIII, I B, II B, III A, IV A, V A and VI A.

In general, the catalysts are preferably used in the form of unsupported catalysts in the novel process. The term "unsupported catalyst" denotes a catalyst which consists only of catalytically active material and, if required, a molding assistant, e.g. graphite or stearic acid, if the catalyst is used in the form of moldings.

In this context, oxygen-containing compounds of titanium, e.g. $TiO_2$, oxygen-containing compounds of aluminum, e.g. $Al_2O_3$, oxygen-containing compounds of zirconium, e.g. $ZrO_2$, and oxygen-containing compounds of silicon, e.g. $SiO_2$, are considered as belonging to the catalytically active material.

The catalysts are arranged as suitable moldings—for example as pellets, spheres, cylinders, rings or extrudates—in the reactor.

The stated concentrations (in % by weight) of the components of the catalyst relate in each case—unless stated otherwise—to the catalytically active material of the prepared catalyst after calcination for one hour at 900° C. and before its reduction with hydrogen.

The catalytically active material of the catalyst, after its final heat treatment and before its reduction with hydrogen, is defined as the sum of the masses of the catalytically active components and essentially contains the catalytically active components copper (metallic), which was added before the shaping of the catalyst material, oxygen-containing compounds of copper and of titanium and optionally oxygen-containing compounds of aluminum and/or of zirconium and/or of silicon.

The sum of the abovementioned essential catalytically active components—calculated as CuO in the case of the oxygen-containing compounds of copper, calculated as $TiO_2$ in the case of the oxygen-containing compounds of titanium and calculated as $Al_2O_3$ and $ZrO_2$ and $SiO_2$ in the case of the oxygen-containing compounds of aluminum and of zirconium and of silicon, respectively—is usually from 70 to 100, preferably from 80 to 100, particularly preferably from 90 to 100, very particularly preferably greater than 95, % by weight, for example 100% by weight.

For the preparation of the novel catalysts, copper compounds and, if required, one or more compounds of the elements selected from the groups I A, II A, III B, IV B, V B, VI B, VIII, I B, II B, III A, IV A, V A and VI A of the Periodic Table are first applied to an inorganic material containing $TiO_2$ and, if required, $Al_2O_3$ and/or $ZrO_2$ and/or $SiO_2$, there being no restrictions at all regarding the method of application. Preferably, the abovementioned inorganic material essentially comprises (i.e. to more than 95% by weight) or consists exclusively of $TiO_2$.

The following methods of application are particularly suitable:

a) Impregnation

Application of a copper salt solution in one or more impregnation stages to the inorganic material. The material is dried and, if required, calcined after the impregnation.

a1) The impregnation can be carried out by the incipient wetness method in which the inorganic material, depending on its water absorptivity, is moistened to not more than saturation with the impregnating solution. However, the impregnation may also be effected in supernatant solution.

a2) In the case of multistage impregnation methods, it is expedient to dry and, if required, to calcine between individual impregnation steps. The multistage impregnation can be particularly advantageously used when a relatively large amount of copper is to be applied to the inorganic material.

a3) The inorganic material is used in the impregnation particularly preferably in the form of a powder. However, it is also possible to use the inorganic material in the form of moldings, for example spheres, extrudates or pellets, which already contain metallic copper powder.

a4) Concentrated aqueous ammonia solution is preferably used as a solvent for the copper salts.

a5) Compounds of the elements selected from the groups I A, II A, III B, IV B, V B, VI B, VIII, I B, II B, III A, IV A, V A and VI A (promoters) can be introduced in a step analogous to a1) by impregnation with a copper- and promoter-containing impregnating solution or in a plurality of stages analogous to a2) by alternate impregnation with copper-containing impregnating solution and promoter-containing impregnating solution.

b) Precipitation

Precipitation of a copper salt solution onto the inorganic material. In a particularly preferred embodiment, this is present as powder in an aqueous suspension.

b1) In one embodiment (i) a copper salt solution is precipitated, preferably with sodium carbonate solution. An aqueous suspension of the inorganic material is initially taken.

b2) In a further embodiment (ii) the titanium-containing inorganic material is prepared in a first step by hydrolysis of a soluble titanium compound, for example a titanium alcoholate, such as titanium tetraisopropylate. This can be further processed either directly or after aging in the aqueous solution with heating (at from 30 to 100° C.) and isolation and washing, and if required drying and/or calcination.

The $TiO_x(OH)_y$-containing intermediate thus prepared is then suspended again in water and the active component is applied analogously to b1).

b3) In a further embodiment (iii) the catalyst raw material can be prepared by combined hydrolysis of a soluble titanium compound (cf. b2) and precipitation of a copper salt solution with sodium carbonate solution (cf. b1). For this purpose, for example, water is initially taken and the three solutions 'soluble titanium compound', 'copper salt solution' and 'sodium carbonate solution' are added simultaneously. Further variations are possible.

b4) In a further embodiment (iv) the precipitated catalyst can be prepared in a two-stage process. In a first stage, a powder is prepared according to a) and is dried. This powder is transferred to an aqueous suspension and is used as an initially taken material equivalent to that described in embodiment (i).

b5) The introduction of promoters can be effected in one step analogous to b1–b3) by precipitation of a copper- and promoter-containing solution or in a plurality of stages analogous to b4) by successive precipitation of a copper-containing solution and promoter-containing solution. In the last-mentioned case, the individual precipitations can be effected directly in succession or can be separated by a wash process and/or drying process and/or calcination process.

In principle, all Cu(I) and/or Cu(II) salts and promoter salts soluble in the solvents used in the application, for example sulfates, nitrates, chlorides, carbonates, acetates, oxalates or ammonium complexes, may be used as starting substances for a) and/or b). Copper carbonate is particularly preferably used for processes according to a) and copper nitrate for processes according to b).

Precipitates which result from a) or b) are filtered in a conventional manner and preferably washed alkali-free.

It is also possible to introduce a promoter component in a suitable form into the filtered and, if required, washed precipitate. Suitable forms are, for example, inorganic salts or complexes or organic compounds.

Both the end products from a) and those from b) are dried at from 50 to 150° C., preferably from 100 to 140° C., and then heated over a period of several hours, for example about 2 hours, at relatively high temperature, i.e. in general from 200 to 400° C., in particular from 200 to 220° C.

It is possible to introduce a promoter component in suitable form both after the drying and after the heating. Suitable forms are, for example, inorganic salts or complexes or organic compounds. The introduction is expediently effected by thorough mixing, kneading and/or compaction, and, if required, liquids, for example water or alcohols, may also be added. After the introduction of the promoter component, a further drying and/or heating step is expediently carried out. In the case of addition in the dry state, however, this may also be dispensed with.

For the preparation of the catalysts used in the novel process, the dried and powdered catalyst material described is shaped into moldings, preferably pellets or extrudates. According to the invention, metallic copper, preferably in finely particulate form, for example a powder, is added as an assistant for shaping the catalyst material.

Preferably from 2 to 40, especially from 5 to 34, particularly preferably from 11 to 28, % by weight, based on the weight of catalytically active material of the dried catalyst material described above, of metallic copper are added.

The copper used generally has a particle diameter of from 1 to 100 µm, preferably from 5 to 30 µm.

For example graphite, preferably in an amount of from about 2 to 4% by weight, based on the weight of the catalyst material, can be added as a further assistant for shaping the catalyst material.

The catalyst moldings are heated, preferably for about 2 hours, at from 250 to 600° C., in particular from 300 to 350° C.

It is also possible to introduce a promoter component in suitable form into the catalyst moldings. Suitable forms are, for example, solutions of inorganic salts, complexes or organic compounds. The introduction is expediently followed by further drying at from 50 to 150° C., preferably from 100 to 140° C. Heating at from 250 to 600° C., in particular from 300 to 350° C., for several hours, preferably about two hours, may additionally be carried out.

The addition of metallic copper powder before the shaping of the catalyst material imparts to the catalyst moldings the mechanical stability necessary for preparing, with the chosen catalyst material, a catalyst which is advantageous and can be economically used under the reaction conditions of the reductive amination.

The activation of the heated catalyst with reducing gases is effected either before or after installation in the reactor in which the novel process is carried out.

When the catalyst is used in the oxide form, it is reduced with reducing gases, for example hydrogen, preferably hydrogen/inert gas mixtures, in particular hydrogen/nitrogen mixtures, at from 100 to 300° C., preferably from 150 to 250° C., in particular from 180 to 240° C., before being loaded with the mixture of starting materials. A gas mixture having a hydrogen content of from 1 to 100% by volume is preferably used.

If the catalyst was reduced beforehand as described above, it can be installed directly in the reactor and loaded with the mixture of starting materials under hydrogen pressure.

The specific surface area of the copper in the catalysts used in the novel process is calculated from the $N_2O$ consumption determined by oxidation of surface copper atoms with gaseous $N_2O$ in a heated sample of the catalyst.

For this purpose, the sample is first treated for 4 hours with hydrogen at 10 mbar (10 hPa) at 240° C. Thereafter, the sample is evacuated to a pressure of less than $10^{-3}$ mbar and then treated for 3 hours with $H_2$ at 30 mbar, then evacuated again to less than $10^{-3}$ mbar, treated for 3 hours with $H_2$ at 100 mbar, once again evacuated to less than $10^{-3}$ mbar and then treated again for 3 hours with $H_2$ at 200 mbar, the treatment with hydrogen being carried out in each case at 240° C.

In a second stage, the sample is exposed to $N_2O$ at 70° C. and 266 mbar for 2 hours, decomposition of the $N_2O$ on the sample being observed. Thereafter, the sample is evacuated to less than $10^{-3}$ mbar and the increase in the mass of the catalyst due to the formation of copper oxide on the surface thereof is then determined.

The specific surface area, measured in this manner, of the copper in the catalysts is in general not more than 10, preferably from 0.1 to 10, more preferably from 0.5 to 7, in particular from 0.5 to 5, m²/g, the mass of the catalyst (in g) being based on the catalyst in the oxide form, i.e. before its reduction with hydrogen.

The mechanical resistance, i.e. the hardness, of the molded catalysts used in the novel process is determined by means of the side crushing strength. For this purpose, the catalyst molding, for example the catalyst pellet, is loaded with increasing force between two parallel plates, it being possible to apply the force, for example, to the lateral surface of catalyst pellets until the catalyst molding breaks. The force recorded on breaking of the catalyst molding is the side crushing strength.

Amines of the formula I where $R^1$ and $R^2$ are each hydrogen, $C_{1-20}$-alkyl, $C_{3-12}$-cycloalkyl, aryl, $C_{7-20}$-aralkyl or $C_{7-20}$-alkylaryl or together are $(CH_2)_j$-X-$(CH_2)_k$, $R^3$ and $R^4$ are each hydrogen, alkyl, such as $C_{1-200}$-alkyl, cycloalkyl such as $C_{3-12}$-cycloalkyl, hydroxyalkyl, such as $C_{1-20}$-hydroxyalkyl, aminoalkyl, such as $C_{1-20}$-aminoalkyl, alkanolaminoalkyl, such as $C_{1-20}$-alkanolaminoalkyl, alkoxyalkyl, such as $C_{2-30}$-alkoxyalkyl, dialkylaminoalkyl, such as $C_{3-30}$-dialkylaminoalkyl, alkylaminoalkyl, such as $C_{2-30}$-alkylaminoalkyl, $R^5$-$(OCR^6R^7CR^8R^9)_n$-$(OCR^6R^7)$, aryl, heteroaryl, aralkyl, such as $C_{7-20}$-aralkyl, heteroaralkyl, such as $C_{4-20}$-hetarylalkyl, alkylaryl, such as $C_{7-20}$-alkylaryl, alkylhetaryl, such as $C_{4-20}$-alkylhetaryl or Y-$(CH_2)_m$-$NR^5$-$(CH_2)_q$ or together are $(CH_2)_1$-X-$(CH_2)_m$ or $R^2$ and $R^4$ together are $(CH_2)_1$-X-$(CH_2)_m$, $R^5$ and $R^{10}$ are each hydrogen, $C_{1-4}$-alkyl or $C_{7-40}$-alkylphenyl, $R^6$, $R^7$, $R^8$ and $R^9$ are each hydrogen, methyl or ethyl,

X is $CH_2$, $CHR^5$, oxygen (O) or $NR^5$,

Y is $N(R^{10})_2$, hydroxyl, $C_{2-20}$-alkylaminoalkyl or $C_{3-20}$-dialkylaminoalkyl, n is an integer from 1 to 30 and j, k, l, m and q are each an integer from 1 to 4, and diamines of the formula IV (IV)

where

Z is a $C_{2-12}$-alkylene chain which is unsubstituted or monosubstituted to trisubstituted by $C_{1-20}$-alkyl, $C_{1-20}$-alkoxy and/or $C_{2-20}$-dialkylamino and may be interrupted once or twice by oxygen or $NR^5$ and

$R^1$, $R^2$, $R^3$, $R^4$ and $R^5$ are as defined above, are commercially of particular interest.

The novel process is therefore preferably used for the preparation of the amines I and diamines IV by reacting primary or secondary alcohols of the formula II or V, respectively, (II)

(V)

or aldehydes or ketones of the formula VI or VII, respectively, (VI)

(VII)

with nitrogen compounds of the formula III (III)

where $R^1$, $R^2$, $R^3$, $R^4$ and Z have the abovementioned meanings.

As is evident from the definitions of $R^2$ and $R^4$, the reaction may also be effected as an intramolecular reaction in a corresponding aminoalcohol, aminoketone or aminoaldehyde.

$R^1$, $R^2$, $R^3$, $R^4$, $R^5$, $R^6$, $R^7$, $R^8$, $R^9$, $R^{10}$, X, Y, Z, j, k, l, m, n a q in the compounds I, II, III, IV and V have, independently of one another, the following meanings:

$R^1$, $R^2$, $R^3$, $R^4$, $R^5$, $R^6$, $R^7$, $R^8$, $R^9$ and $R^{10}$ are each hydrogen (H), $R^3$ and $R^4$ are each $C_{1-200}$-alkyl, preferably $C_{1-14}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl or 3-n-butyl-n-nonyl, particularly preferably isopropyl, 2-ethylhexyl, n-decyl, 2-n-propyl-n-heptyl, n-tridecyl, 2-n-butyl-n-nonyl or 3-n-butyl-n-nonyl, or preferably $C_{40-200}$-alkyl, such as polybutyl, polyisobutyl, polypropyl, polyisopropyl or polyethyl, particularly preferably polybutyl or polyisobutyl, $C_{1-20}$-hydroxyalkyl, preferably $C_{1-8}$-hydroxyalkyl, particularly preferably $C_{1-4}$-hydroxyalkyl, such as hydroxymethyl, 1-hydroxyethyl, 2-hydroxyethyl, 1-hydroxy-n-propyl, 2-hydroxy-n-propyl, 3-hydroxy-n-propyl or 1-hydroxymethylethyl, $C_{1-20}$-aminoalkyl, preferably $C_{1-8}$-aminoalkyl, such as aminomethyl, 2-aminoethyl, 2-amino-1,1-dimethylethyl, 2-amino-n-propyl, 3-amino-n-propyl, 4-amino-n-butyl, 5-amino-n-pentyl, N-(aminoethyl) aminoethyl or N-(aminoethyl)aminomethyl, $C_{1-20}$-hydroxyalkylaminoalkyl, preferably $C_{1-8}$-hydroxyalkylaminoalkyl, such as (2-hydroxyethylamino)methyl, 2-(2-hydroxyethylamino)ethyl or 3-(2-hydroxyethylamino) propyl, $C_{2-30}$-alkoxyalkyl, preferably $C_{2-20}$-alkoxyalkyl, particularly preferably $C_{2-8}$-alkoxyalkyl, such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl or 2-methoxyethyl, particularly preferably $C_2$- to $C_4$-alkoxyalkyl, such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl or 2-methoxyethyl, $R^5$-$(OCR^6R^7CR^8R^9)_n$-$(OCR^6R^7)$, preferably $R^5$-$(OCHR^7CHR^9)_n$-$(OCR^6R^7)$, particularly preferably $R^5$-$(OCH_2CHR^9)_n$-$(OCR^6R^7)$, $C_{3-30}$-dialkylaminoalkyl, preferably $C_{3-20}$-dialkylaminoalkyl, particularly preferably $C_{3-10}$-N,N-dialkylaminoalkyl, such as N,N-dimethylaminomethyl, 2-(N,N-dibutylamino)methyl, 2-(N,N-dimethylamino) ethyl, 2-(N,N-diethylamino)ethyl, 2-(N,N-dibutylamino)ethyl, 2-(N,N-di-n-propylamino) ethyl or 2-(N,N-diisopropylamino)ethyl, or $(R^5)_2N$-$(CH_2)_q$, $C_{2-30}$-alkylaminoalkyl, preferably $C_{2-20}$-alkylaminoalkyl, particularly preferably $C_{2-8}$-alkylaminoalkyl, such as methylaminomethyl, methylaminoethyl, ethylaminomethyl, ethylaminoethyl or isopropylaminoethyl, or $(R^5)HN$-$(CH_2)_q$, Y-$(CH_2)_m$-$NR^5$-$(CH_2)_q$, $C_{4-20}$-hetarylalkyl, such as pyrid-2-yl-methyl, furan-2-yl-methyl, pyrrol-3-yl-methyl or imidazol-2-yl-methyl, $C_{4-20}$-alkylhetaryl, such as 2-methyl-3-pyridyl, 4,5-dimethyl-imidazol-2-yl, 3-methyl-2-furanyl or 5-methyl-2-pyrazinyl, hetaryl, such as 2-pyridyl, 3-pyridyl, 4-pyridyl, pyrazinyl, pyrrol-3-yl, imidazol-2-yl, 2-furanyl or 3-furanyl, $R^1$, $R^2$, $R^3$ and $R^4$ are each $C_{3-12}$-cycloalkyl, preferably $C_{3-8}$-cycloalkyl, such as cyclopropyl, cyclobutyl, cyclopentyl, cyclohexyl, cycloheptyl or cyclooctyl, particularly preferably cyclopentyl, cyclohexyl or cyclooctyl, aryl, such as phenyl, 1-naphthyl, 2-naphthyl, 1-anthryl, 2-anthryl or 9-anthryl, preferably phenyl, 1-naphthyl or 2-naphthyl, particularly preferably phenyl, $C_{7-20}$-alkylaryl, preferably $C_{7-12}$-alkylphenyl, such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl or 4-n-propylphenyl, $C_{7-20}$-aralkyl, preferably $C_{7-12}$-phenylalkyl, such as benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl or 4-phenylbutyl, or particularly preferably benzyl, 1-phenethyl or 2-phenethyl, $R^3$ and $R^4$ or $R^2$ and $R^4$ together are a $-(CH_2)_l-X-(CH_2)_m-$ group, such as $-(CH_2)_3-$, $-(CH_2)_4-$, $-(CH_2)_5-$, $-(CH_2)_6-$, $-(CH_2)_7-$, $-(CH_2)-O-(CH_2)_2-$, $-(CH_2)-NR^5-(CH_2)_2-$, $-(CH_2)_2-O-(CH_2)_2-$, $-(CH_2)_2-NR^5-(CH_2)_2-$, $-CH_2-O-(CH_2)_3-$ or $-CH_2-NR^5-(CH_2)_3-$, $R^1$ and $R^2$ are each $C_{1-20}$-alkyl, preferably $C_{1-8}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl or isooctyl, particularly preferably $C_{1-4}$-alkyl, such as methyl, ethyl, n-propyl, isopropyl, n-butyl, isobutyl, sec-butyl or tert-butyl, $R^1$ and $R^2$ together are a $-(CH_2)_j-X-(CH_2)_k-$ group, such as $-(CH_2)_3-$, $-(CH_2)_4-$, $-(CH_2)_5-$, $-(CH_2)_6-$, $-(CH_2)_7-$, $-(CH_2)-O-(CH_2)_2-$, $-(CH_2)-NR^5-(CH_2)_2-1-(CH_2)_2-O-(CH_2)_2-$, $-(CH_2)_2-NR^5-(CH_2)_2-$, $-CH_2-O-(CR_2)_3-$ or $-CH_2-NR^5-(CH_2)_3-$, $R^5$ and $R^{10}$ are each $C_{1-4}$-alkyl, such as methyl, ethyl, n-propyl, isopropyl, n-butyl, isobutyl, sec-butyl or tert-butyl, preferably methyl or ethyl, particularly preferably methyl, $C_{7-40}$-alkylphenyl, such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-, 3- or 4-nonylphenyl, 2-, 3- or 4-decylphenyl, 2,3-, 2,4-, 2,5-, 3,4- or 3,5-dinonylphenyl or 2,3-, 2,4-, 2,5-, 3,4- or 3,5-didecylphenyl, $R^6$, $R^7$, $R^8$ and $R^9$ are each methyl or ethyl, preferably methyl, X is $CH_2$, $CHR^5$, oxygen or $NR^5$, Y is $N(R^{10})_2$, hydroxyl, $C_{2-20}$-alkylaminoalkyl, preferably $C_{2-16}$-alkylaminoalkyl, such as methylaminomethyl, methylaminoethyl, ethylaminomethyl, ethylaminoethyl or isopropylaminoethyl, $C_{3-20}$-dialkylaminoalkyl, preferably $C_{3-16}$-dialkylaminoalkyl, such as dimethylaminomethyl, dimethylaminoethyl, dialkylaminoethyl, di-n-propylaminoethyl or diisopropylaminoethyl, Z is a $C_{2-12}$-alkylene chain, preferably a $C_{2-8}$-alkylene chain, which may be interrupted once or twice by oxygen or $NR^5$, such as $-(CH_2)_3-$, $-(CH_2)_4-$, $-(CH_2)_5-$, $-(CH_2)_6-$, $-(CH_2)_7-$, $-(CH_2)-O-(CH_2)_2-$, $-(CH_2)-NR^5-(CH_2)_2-$, $-(CH_2)_2-O-(CH_2)_2-$, $-(CH_2)_2-NR^5-(CH_2)_2-$, $-CH_2-O-(CH_2)_3-$, $-CH_2-NR^5-(CH_2)_3-$, and which may carry from one to three substituents which are inert under the reaction conditions, such as $C_{1-20}$-alkyl, $C_{1-20}$-alkoxy or $C_{2-20}$-dialkylamino, where $C_{1-20}$-alkyl is as defined above for $R^1$ and $R^2$, $C_{1-20}$-alkoxy is preferably $C_{1-8}$-alkoxy, such as methoxy, ethoxy, n-propoxy, isopropoxy, n-butoxy, isobutoxy, sec-butoxy, tert-butoxy, n-pentyloxy, isopentyloxy, sec-pentyloxy, neopentyloxy, 1,2-dimethylpropoxy, n-hexyloxy, isohexyloxy, sec-hexyloxy, n-heptyloxy, isoheptyloxy, n-octyloxy or isooctyloxy, and $C_{2-20}$-dialkylamino is preferably $C_{2-12}$-dialkylamino, in particular $C_{2-8}$-dialkylamino, such as dimethylamino, diethylamino, di-n-propylamino, diisopropylamino, di-n-butylamino, N-ethyl-N-methylamino, N-methyl-N-n-propylamino, N-methyl-N-isopropylamino, or dicyclohexylamino, for example $-CH_2-CHCH_3-O-CHCH_3-CH_2-$, $-(CH_2)_2-CH(OCH_3)-(CH_2)_2-$, $-(CH_2)_2-CH(OC_2H_5)-(CH_2)_2-$, $-(CH_2)-CHCH_3-(CH_2)_2-$, $-(CH_2)_2-CHCH_3-(CH_2)_2-$, $-CH_2-CHCH_3-(CH_2)_3-$, $-(CH_2)-CHCH_3-(CH_2)_2-$ or $-(CH_2)_2-CH(N(CH_3)_2)-(CH_2)_2-$, j and l are each an integer from 1 to 4, such as 1, 2, 3 or 4, preferably 2 or 3, particularly preferably 2, k, m and q are each an integer from 1 to 4, such as 1, 2, 3 or 4, preferably 2, 3 or 4, particularly preferably 2 or 3, n is an integer from 1 to 10, preferably an integer from 1 to 8, such as 1, 2, 3, 4, 5, 6, 7 or 8, particularly preferably an integer from 1 to 6, such as 1, 2, 3, 4, 5 or 6.

Suitable alcohols are virtually all primary and secondary aliphatic alcohols. The aliphatic alcohols may be straight-chain, branched or cyclic. Secondary alcohols are aminated just as primary alcohols. There are virtually no restrictions to the number of carbon atoms of the alcohols capable of amination. The alcohols may furthermore carry substituents which are inert under the conditions of the amination with hydrogenation, for example alkoxy, alkyleneoxy, alkylamino or dialkylamino. If polyhydric alcohols are to be aminated, it is possible, by controlling the reaction conditions, to obtain aminoalcohols, cyclic amines or polyaminated products.

The amination of 1,4-diols leads to 1-amino-4-hydroxy or 1,4-diamino compounds or to pyrrolidines, depending on the choice of the reaction conditions.

The amination of 1,6-diols leads to 1-amino-6-hydroxy or 1,6-diamino compounds or to hexamethyleneimines, depending on the choice of the reaction conditions.

The amination of 1,5-diols leads to 1-amino-5-hydroxy or 1,5-diamino compounds or to piperidines, depending on the choice of the reaction conditions. Accordingly, monoaminodiglycol (=ADG =$H_2N-CH_2CH_2-O-CH_2CH_2-OH$), diaminodiglycol or particularly preferably morpholine can be obtained from diglycol by amination with $NH_3$. Correspondingly, piperazine is particularly preferably obtained from diethanolamine. N-(2-Hydroxyethyl) piperazine can be obtained from triethanolamine.

For example, the following alcohols are preferably aminated:

methanol, ethanol, n-propanol, isopropanol, n-butanol, isobutanol, n-pentanol, n-hexanol, 2-ethylhexanol, tridecanol, stearyl alcohol, palmityl alcohol, cyclobutanol, cyclopentanol, cyclohexanol, benzyl alcohol, 2-phenyl-ethanol, 2-(p-methoxyphenyl)ethanol, 2-(3,4-dimethoxyphenyl)ethanol, 1-phenyl-3-butanol, ethanolamine, n-propanolamine, isopropanolamine, 2-amino-1-propanol, 1-methoxy-2-propanol, 3-amino-2,2-dimethyl-1-propanol, n-pentanolamine (1-amino-5-pentanol), n-hexanolamine (1-amino-6-hexanol), ethanolamine, diethanolamine, triethanolamine, N-alkyldiethanolamines, diisopropanolamine, 3-(2-hydroxyethylamino)propan-1-ol, 2-(N,N-dimethylamino)ethanol, 2-(N,N-diethylamino)ethanol, 2-(N,N-di-n-propylamino)ethanol, 2-(N,N-di-isopropylamino)ethanol, 2-(N,N-di-n-butylamino)ethanol, 2-(N,N-di-isobutylamino)ethanol, 2-(N,N-di-sec-butylamino)ethanol, 2-(N,N-di-tert-butylamino)ethanol, 3-(N,N-dimethylamino)propanol, 3-(N,N-diethylamino)propanol, 3-(N,N-di-n-propylamino)propanol, 3-(N,N-di-isopropylamino)propanol, 3-(N,N-di-n-butylamino)propanol, 3-(N,N-di-isobutylamino)propanol, 3-(N,N-di-sec-butylamino)propanol, 3-(N,N-di-tert-butylamino)propanol, 1-dimethylamino-4-pentanol, 1-diethylamino-4-pentanol, ethylene glycol, 1,2-propylene glycol, 1,3-propylene glycol, diglycol, 1,4-butanediol, 1,5-pentanediol, 1,6-hexanediol, 2,2-bis[4-hydroxycyclohexyl]propane, methoxyethanol, propoxyethanol, butoxyethanol, polyisobutyl alcohols, polypropyl alcohols, polyethylene glycol ethers, polypropylene glycol ethers and polybutylene glycol ethers. In the novel reaction, the last-mentioned polyalkylene glycol ethers are converted into the corresponding amines by conversion of their free hydroxyl groups.

Particularly preferred alcohols are methanol, ethanol, n-propanol, isopropanol, n-butanol, sec-butanol, tert-butanol, fatty alcohols, ethylene glycol, diethylene glycol, N-methyldiethanolamine and 2-(2-dimethylaminoethoxy)ethanol.

Suitable aldehydes and ketones are virtually all aliphatic or aromatic aldehydes and ketones. The aldehydes and ketones may be straight-chain, branched or cyclic. There are virtually no restrictions to the number of carbon atoms of the aldehydes and ketones capable of amination. The aldehydes and ketones may furthermore carry substituents which are inert under the conditions of the amination with hydrogenation, for example alkoxy, alkyleneoxy, alkylamino or dialkylamino. If di- or oligoaldehydes or di- or oligoketones are to be subjected to reductive amination, it is possible, by controlling the reaction conditions, to obtain aminoaldehydes or aminoketones, cyclic amines or products which have undergone reductive polyamination.

For example, the following aldehydes and ketones are preferably subjected to reductive amination:

formaldehyde, acetaldehyde, propionaldehyde, n-butyraldehyde, isobutyraldehyde, n-pentanal, n-hexanal, 2-ethylhexanal, 2-methylpentanal, 3-methylpentanal, 4-methylpentanal, glyoxal, benzaldehyde, p-methoxybenzaldehyde, p-methylbenzaldehyde, phenylacetaldehyde, (p-methoxyphenyl)acetaldehyde, (3,4-dimethoxyphenyl)acetaldehyde, furfural, 4-formyltetrahydropyran, 3-formyltetrahydrofuran, 5-formylvaleronitrile, hydroformylated polyisobutene (polyisobutene aldehyde, PIBA), oligomer obtained by metathesis of 1-pentene and cyclopentene and hydroformylated, acetone, 2-butanone, 3-methylbutan-2-one, 4-methylpentan-2-one, diethyl ketone, tetralone, acetophenone, p-methylacetophenone, p-methoxyacetophenone, m-methoxyacetophenone, 1-acetylnaphthalene, 2-acetylnaphthalene, 1-phenyl-3-butanone, benzophenone, cyclobutanone, cyclopentanone, cyclopentenone, cyclohexanone, cyclohexenone and 2,6-dimethylcyclohexanone.

Both ammonia and primary and secondary, aliphatic or cycloaliphatic or aromatic amines may be used as aminating agents in the amination of alcohols, aldehydes or ketones in the presence of hydrogen.

When ammonia is used as the aminating agent, the alcoholic hydroxyl group or the aldehyde group or the keto group is first converted into the primary amino group (-NH$_2$). The primary amine thus formed can react with further alcohol or aldehyde or ketone to give the corresponding secondary amine and this in turn can react with further alcohol or aldehyde or ketone to give the corresponding, preferably symmetrical, tertiary amine. Depending on the composition of the reaction batch and depending on the reaction conditions used (pressure, temperature, reaction time), preferably primary, secondary or tertiary amines can be prepared in this way as desired.

Cyclic amines, e.g. pyrrolidines, piperidines, hexamethyleneimines, piperazines and morpholines, can be prepared in this manner by intramolecular amination with hydrogenation from polyhydric alcohols or di- or oligoaldehydes or di- or oligoketones.

Apart from ammonia, it is possible to use primary or secondary amines as aminating agents.

These aminating agents are preferably used for the preparation of asymmetrically substituted di- or trialkylamines such as ethyl diisopropylamine and ethyl dicyclohexylamine. For example, the following mono- and dialkylamines are used as aminating agents: methylamine, dimethylamine, ethylamine, diethylamine, n-propylamine, di-n-propylamine, isopropylamine, diisopropylamine, isopropylethylamine, n-butylamine, di-n-butylamine, sec-butylamine, di-sec-butylamine, isobutylamine, n-pentylamine, sec-pentylamine, isopentylamine, n-hexylamine, sec-hexylamine, isohexylamine, cyclohexylamine, aniline, toluidine, piperidine, morpholine and pyrrolidine.

The aminating agent may be used in stoichiometric, substoichiometric or superstoichiometric amounts, based on the alcoholic hydroxyl group or aldehyde group or keto group to be aminated.

In the case of amination of alcohols, aldehydes or ketones with primary or secondary amines, the amine is preferably used in roughly stoichiometric amount per mole of alcoholic hydroxyl group, aldehyde group or keto group to be aminated.

In particular, ammonia is generally used in a 1.5- to 250-fold, preferably 5- to 100-fold, in particular 2- to 10-fold molar excess per mole of alcoholic hydroxyl group, aldehyde group or keto group to be reacted.

A larger excess both of ammonia and of primary or secondary amines is possible.

The novel process can be carried out batchwise or, preferably, continuously, the catalyst preferably being arranged as a fixed bed in the reactor.

However, the embodiment in the form of a fluidized-bed reaction with catalyst material moving upward and downward is also possible.

The amination of the primary or secondary alcohol groups, aldehyde groups or keto groups of the starting material can be carried out in the liquid phase or in the gas phase. The fixed-bed process in the gas phase is preferred.

When the liquid phase is employed, the starting materials (alcohol, aldehyde or ketone plus amine), including hydrogen, are passed simultaneously in the liquid phase at from 5 to 30 MPa (50–300 bar), preferably from 5 to 25 MPa, particularly preferably from 15 to 25 MPa, and from 120 to 350° C., preferably from 130 to 250° C., particularly preferably from 180 to 230° C., over the catalyst, which is usually present in a fixed-bed reactor, preferably heated from the outside. Both a trickle-bed procedure and a liquid-phase procedure are possible. The catalyst space velocity is generally from 0.05 to 5, preferably from 0.1 to 2, particularly preferably from 0.2 to 0.6, kg of alcohol, aldehyde or ketone per liter of catalyst (bulk volume) per hour. If required, the starting materials may be diluted with a suitable solvent such as tetrahydrofuran, dioxane, N-methylpyrrolidone or ethylene glycol dimethyl ether. It is expedient to heat the reactants before they are fed into the reaction vessel, and preferably to do so to the reaction temperature.

When the gas phase is employed, the gaseous starting materials (alcohol, aldehyde or ketone plus amine) are passed, in a gas stream, preferably hydrogen, chosen to be sufficiently large for vaporization, at from 0.1 to 40 MPa (from 1 to 400 bar), preferably from 0.1 to 10 MPa, but particularly preferably from 0.1 to 5 MPa, in the presence of hydrogen, over the catalyst. The temperatures for the amination of alcohols are in general from 80 to 300° C, preferably from 120 to 270° C., particularly preferably from 160 to 250° C. The amination of aldehydes or ketones differs in terms of procedure from the amination of alcohols only in the fact that at least stoichiometric amounts of hydrogen must be present and that the reaction temperatures are in general from 80 to 300° C., preferably from 100 to 250° C. The flow over the fixed catalyst bed may be either from above or from below. The required gas stream is obtained preferably by a circulation procedure.

The catalyst space velocity is in general from 0.01 to 2, preferably from 0.05 to 0.5, kg of alcohol, aldehyde or ketone per liter of catalyst (bulk volume) per hour.

Hydrogen is fed to the reaction in general in an amount of from 5 to 400, preferably from 50 to 200, 1 per mole of alcohol, aldehyde or ketone component, the data in liters being converted in each case to standard temperature and pressure conditions (S.T.P.).

Both when the liquid phase is employed and when the gas phase is employed, it is possible to use relatively high temperatures and relatively high total pressures. The pressure in the reaction vessel, which is the sum of the partial pressures of the aminating agent, of the alcohol, aldehyde or ketone and of the reaction products formed and of any solvent present at the stated temperatures, is expediently increased to the desired reaction pressure by forcing in hydrogen.

Both in the continuous procedure in the liquid phase and in the continuous procedure in the gas phase, the excess aminating agent can be circulated together with the hydrogen.

If the catalyst is arranged as a fixed bed, it may be advantageous for the selectivity of the reaction to mix the catalyst moldings in the reactor with inert packings, i.e. to "dilute" them. The amount of packings in such catalyst formulations may be from 20 to 80, in particular from 30 to 60, especially from 40 to 50, parts by volume.

The water of reaction formed in the course of the reaction (in each case one mole per mole of converted alcohol group, aldehyde group or keto group) generally does not adversely affect the conversion, the reaction rate, the selectivity and the catalyst life and is therefore expediently not removed from the reaction product until the latter is worked up, said removal being effected, for example, by distillation.

The excess aminating agent and the hydrogen are removed from the reacted mixture, expediently after it has been let down, and the amination products obtained are purified by distillation or rectification, liquid extraction or crystallization. The excess aminating agent and the hydrogen are advantageously recycled to the reaction zone. The same applies to any incompletely converted alcohol, aldehyde or ketone component.

EXAMPLES

Catalyst preparations

All percentages stated in the catalyst preparations are percentages by weight, unless stated otherwise. The stated percentage compositions are based on the oxidic components of the prepared catalysts after calcining for one hour at 900° C.

Catalyst A (comparative catalyst)

Catalyst A was prepared by precipitating a solution of copper nitrate and aluminum nitrate with sodium carbonate solution according to DT-A-24 45 303, example 1, except that the Cu/Al atomic ratio was brought to 0.7 (instead of 0.84). The resulting precipitated material was filtered off, washed, and dried at 120° C. The dried powder was calcined for two hours at 250 C and then compressed with 3% of graphite to give pellets having a diameter of 5 mm. These pellets were heated for 2 hours at 580° C. The prepared catalyst contained 53% of Cu, calculated as CuO, and 47% of $Al_2O_3$ and had a bulk density of 1090 g/l, a BET surface area of 101 $m^2/g$, a copper surface area of 11.5 $m^2/g$ and a hydrogen absorption of 0.41 ml/g.

Catalyst B

Catalyst B was prepared by precipitating an aqueous solution of copper nitrate (containing 15.5% by weight of Cu) with aqueous sodium carbonate solution (containing 20% by weight of $Na_2CO_3$). A suspension of $TiO_2$ in water (690 ml of $H_2O$ per 100 g of $TiO_2$) was used as the initially taken mixture. The precipitated material formed during the precipitation was filtered off, washed, and dried at 120° C. The dried powder was calcined for two hours at 220° C. and then compressed (molded) with metallic copper powder and 3% of graphite to give pellets having a diameter of 3 mm. These pellets were heated for 2 hours at 330° C. The prepared catalyst contained 24% of precipitated Cu, calculated as CuO, 16% of metallic Cu, which was introduced before the molding procedure, and 56% of $TiO_2$ and had a bulk density of 1820 g/l, a BET surface area of 125 $m^2/g$, a copper surface area of 2.0 $m^2/g$ and a water absorption of 0.1 ml/g.

Catalyst D

Catalyst D was prepared by precipitating an aqueous solution of copper nitrate (containing 15.5% by weight of Cu) with aqueous sodium carbonate solution (containing 20% by weight of $Na_2CO_3$). A suspension of $TiO_2$ in water (690 ml of $H_2O$ per 100 g of $TiO_2$) was used as the initially taken mixture, less $TiO_2$ being initially taken and more malachite being precipitated in comparison with the preparation of catalyst B. The precipitated material formed during the precipitation was filtered off, washed, and dried at 120° C. The dried powder was calcined for two hours at 200° C. and then compressed (molded) with metallic copper powder and 3% of graphite to give pellets having a diameter of 3 mm. These pellets were heated for 2 hours at 330° C. The prepared catalyst contained 42% of precipitated Cu, calculated as CuO, 16% of metallic Cu, which was introduced before the molding procedure, and 38% of $TiO_2$ and had a bulk density of 1900 g/l, a BET surface area of 74 $m^2/g$, a copper surface area of 2.2 $m^2/g$ and a water absorption of 0.28 ml/g.

Catalyst E (comparative catalyst)

Catalyst E was prepared by precipitating a solution of copper nitrate (containing 15.5% by weight of Cu) with aqueous sodium carbonate solution (containing 20% by weight of $Na_2CO_3$). A suspension of $TiO_2$ in water 1690 ml of $H_2O$ per 100 g of $TiO_2$) was used as the initially taken mixture. The precipitated material formed during the precipitation was filtered off, washed and dried at 120° C. The dried powder was made into a paste with water and compacted in a kneader. Thereafter, drying was carried out again at 120° C. and calcination was effected for two hours at 330° C. The powder was then compressed (molded) with 3% of graphite to give pellets having a diameter of 3 mm. The prepared catalyst contained 53% of CuO and 47% of $TiO_2$ and had a bulk density of 1490 g/l, a BET surface area of 45 $m^2$/g, a copper surface area of 1.8 $m^2$/g and a water absorption of 0.21 ml/g.

Catalyst F

Catalyst F was prepared by precipitating (analogously to catalyst D) an aqueous solution of copper nitrate (containing 15.5% by weight of Cu) with aqueous sodium carbonate solution (containing 20% by weight of $Na_2CO_3$). A suspension of $TiO_2$ in water (690 ml of $H_2O$ per 100 g of $TiO_2$) was used as the initially taken mixture. The precipitated material formed during the precipitation was filtered off, washed, and dried at 120° C. The dried powder was made into a paste with water and compacted in a kneader. Thereafter, drying was carried out again at 120° C. and calcination was effected for two hours at 330° C. The powder was then compressed (molded) with metallic copper powder and 3% of graphite to give pellets having a diameter of 3 mm. The prepared catalyst contained 42% of precipitated Cu, calculated as CuO, 16% of metallic Cu, which was introduced before the molding procedure, and 38% of $TiO_2$ at a bulk density of 1350 g/l, a BET surface area of 44 $m^2$/g, a copper surface area of 1.6 $m^2$/g and a water absorption of 0.24 ml/g.

Catalyst G

Catalyst G was prepared analogously to catalyst D by precipitating an aqueous solution of copper nitrate (containing 15.5% by weight of Cu) with aqueous sodium carbonate solution (containing 20% by weight of $Na_2CO_3$), but with a higher content of precipitated Cu. A suspension of $TiO_2$ in water (690 ml of $H_2O$ per 100 g of $TiO_2$) was used as the initially taken mixture. The precipitated material formed during the precipitation was filtered off, washed, and dried at 120° C. The dried powder was calcined for two hours at 200° C. and then compressed (molded) with metallic copper powder and 3% of graphite to give pellets having a diameter of 3 mm. These pellets were heated for 2 hours at 330° C. The prepared catalyst contained 48% of precipitated Cu, calculated as CuO, 16% of metallic Cu, which was introduced before the molding procedure, and 32% of $TiO_2$ and had a bulk density of 1550 g/l, a BET surface area of 43 $m^2$/g and a water absorption of 0.20 ml/g.

Mechanical properties of the catalysts A, D, E and F:

The side crushing strength was used for characterizing the mechanical properties of the catalysts described. The prepared catalyst was used as described in the examples.

| Catalyst | Side crushing strength (oxidic state) |
| --- | --- |
| Comparative catalyst A | 56 N |
| Catalyst D | 58 N |
| Comparative catalyst E | 27 N |
| Catalyst F | 55 N |

Result:

Comparative catalyst A ($Cu/Al_2O_3$) and the two catalysts D and F ($Cu/TiO_2$) used according to the invention have a side crushing strength of from 50 to 60 Newton. On the other hand, the $Cu/TiO_2$ catalyst E, to which no copper powder was added before pelleting, has a substantially lower side crushing strength of only from 20 to 30 N.

By adding copper powder before the molding of the catalyst material, it is therefore possible substantially to improve the mechanical properties of $Cu/TiO_2$-containing catalysts.

Experimental apparatus

BRIEF DESCRIPTION OF DRAWINGS

Apparatus 1

Apparatus 1 (cf. FIG. 1) as a continuous straight-pass gas-phase apparatus was operated at atmospheric pressure (0 bar gauge pressure) and at from 170 to 200° C. The amount of catalyst used was 100 ml in each case (bulk volume).

Figure 1:
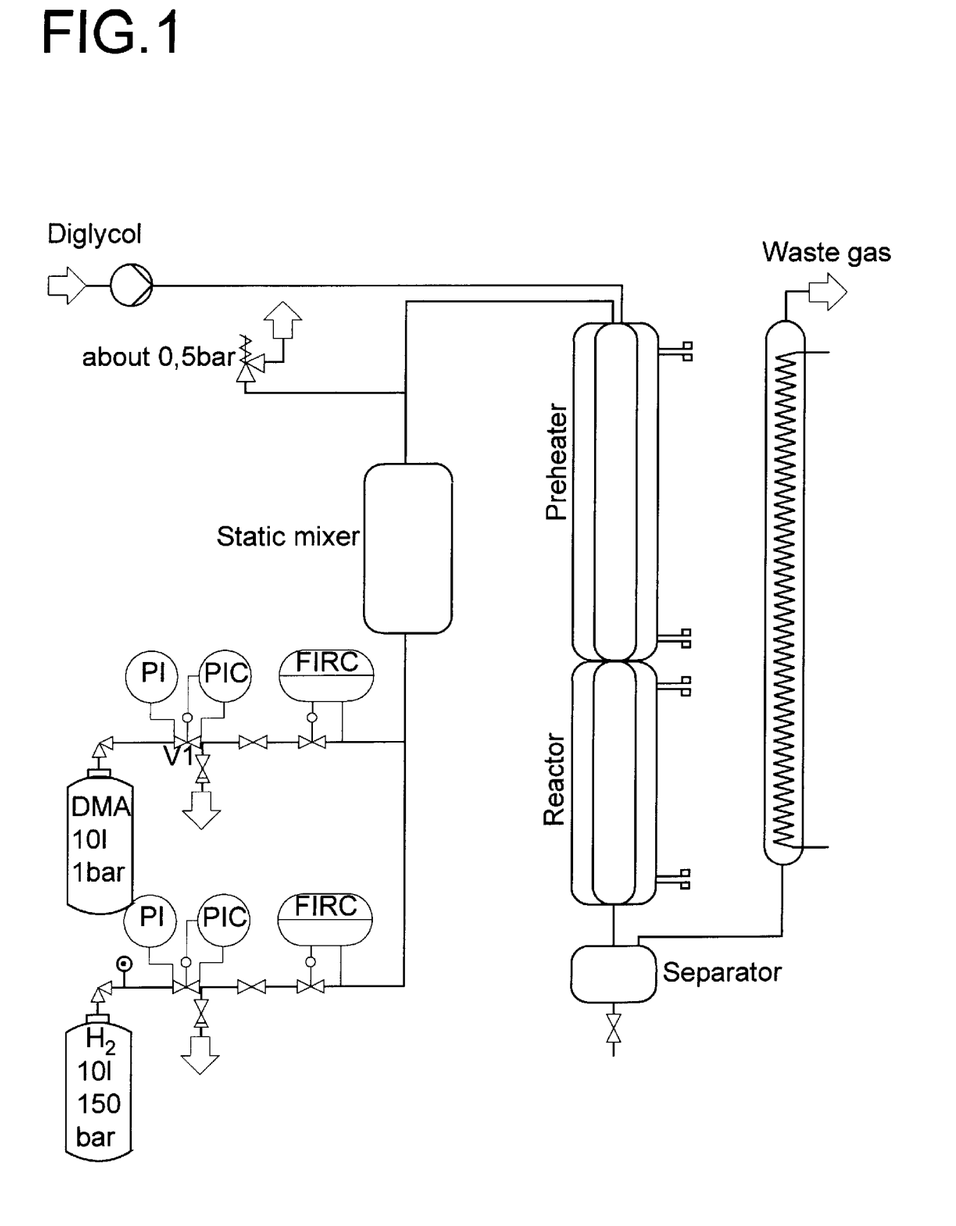

Before the addition of the starting materials, the catalyst was reduced with 4:1 $N_2/H_2$ at 200° C. (4 h) and then with 100% of $H_2$ (4 h).

To permit a comparison, all catalysts were as far as possible tested at an alcohol conversion of about 95% by varying the space velocity and temperature. The gas chromatographic analysis of the reaction products for determining the contents in % by weight was carried out using 1-propanol as an internal standard. Byproducts were identified by GC-MS coupling.

Apparatus 2

Apparatus 2 is a continuous gas-phase pressure apparatus which is equipped with an oil-heated reactor of 16 mm diameter, a separator and a gas circulation. The amount of catalyst used was 100 ml (bulk volume). Amine and fresh hydrogen were fed in with flow control, introduced into the recycled gas and heated to reaction temperature. The preheated alcohol was then fed into this gas mixture with flow control and passed to the heated reactor. The reacted mixture was cooled and was passed into the separator. The major part of the gas phase was circulated. A small part of the gas phase was removed to keep the plant pressure constant. The liquid phase formed was removed with level control and analyzed by means of a gas chromatograph.

Before the starting materials were added, the installed catalyst was reduced in each case at 200° C. in an $H_2/N_2$ stream, the procedure being started with an $H_2/N_2$ ratio of from 1 to 20% by volume and the ratio gradually being increased to pure $H_2$.

Apparatus 3

Figure 2:
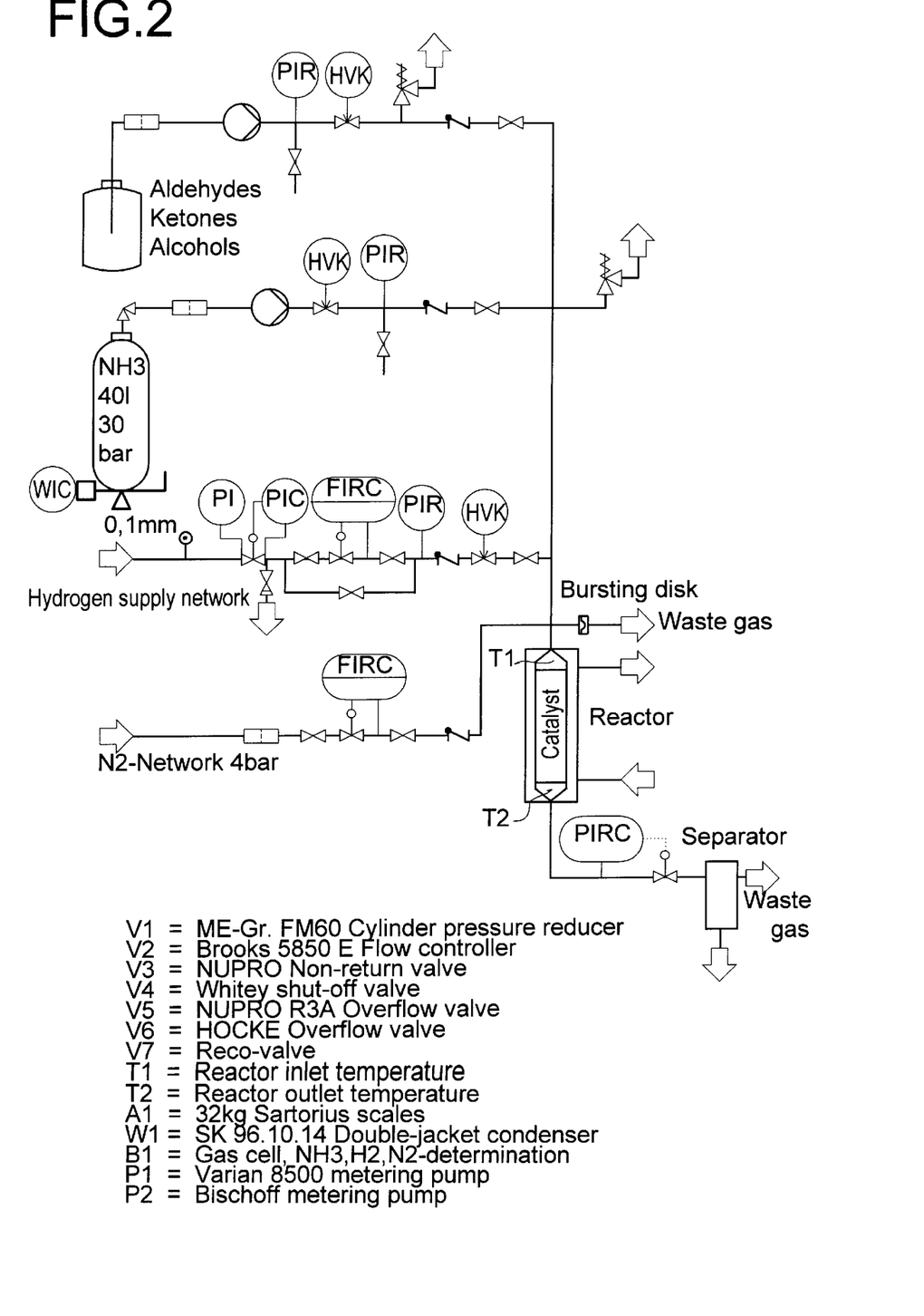

Apparatus 3 (cf. FIG. 2) is a continuous gas-phase pressure apparatus which is equipped with an oil-heated reactor of 8 mm diameter and a separator. The amount of catalyst used was 100 ml (bulk volume). The amination was carried out in a straight pass. The reacted mixture was cooled and was passed into the separator.

EXAMPLE 1

Amination of ethanol with dimethylamine to give dimethylethylamine

Ethanol was reacted with dimethylamine over catalyst B in apparatus 1 to give dimethylethylamine. At about 220° C. and catalyst space velocities of from 0.16 to 0.19 kg of ethanol per 1 of catalyst per h, the desired dimethylethylamine was formed with selectivities of about 70% at ethanol conversions of about 95%. The formation of monomethylethylamine was substantially suppressed (cf. table 1, which shows, inter alia, the content of products in the reacted mixture in GC % by area).

TABLE 1

| T [°C.] | Pressure [bar] | Feeds DMA [g/h] | EtOH [ml/h] | H$_2$ [¹(S.T.P.)/h] | Space velocity [g/l * h] | DMA/EtOH mol/mol | Sample No. | MA 2.24 % by area | DMA 2.35 % by area | TMA 2.58 % by area | EtOH 2.73 % by area | MEA 2.73 % by area | DMEA 3.46 % by area | MDEA 5.15 % by area | Total % by area |
|---|---|---|---|---|---|---|---|---|---|---|---|---|---|---|---|
| 199 | 20 | 21.5 | 11 | 15 | 166 | 2.65 | 19 | 2.03 | 41.31 | 8.7 | 4.35 | 3.82 | 39.16 | 0.59 | 99.96 |
| 199 | 20 | 21.1 | 11 | 15 | 174 | 2.48 | 20 | 1.64 | 37.81 | 9.54 | 4.07 | 3.52 | 42.71 | 0.66 | 99.95 |
| 199 | 20 | 21.7 | 11 | 15 | 174 | 2.55 | 21 | 1.64 | 37.08 | 10.27 | 4.13 | 3.49 | 42.72 | 0.65 | 99.98 |
| 199 | 20 | 22 | 12 | 15 | 189 | 2.37 | | | | | | | | | |
| 199 | 20 | 21.6 | 10.5 | 15 | 161 | 2.66 | 22 | 1.91 | 38.58 | 9.68 | 4.23 | 3.65 | 40.9 | 0.64 | 99.59 |
| 199 | 20 | 21.7 | 10.9 | 15 | 172 | 2.57 | 23 | 1.96 | 39.61 | 9.51 | 4.72 | 3.57 | 40 | 0.63 | 100 |
| 199 | 20 | 21.7 | 11 | 15 | 174 | 2.55 | 24 | 1.53 | 37.24 | 10.02 | 4.65 | 3.56 | 42.32 | 0.67 | 99.99 |

Abbreviations used:
DMA = dimethylamine
MA = methylamine
TMA = trimethylamine
MEA = monoethylamine
DMEA = dimethylethylamine
MDEA = methyldiethylamine

EXAMPLE 2

Amination of diethylene glycol with dimethylamine

Diethylene glycol was reacted with dimethylamine over catalyst A (comparative catalyst) and over catalysts D and G in apparatus 1 to give 2-(2-dimethylaminoethoxy)ethanol and bis(2-dimethylaminoethyl) ether (cf. reaction scheme below).

With comparable diethylene glycol conversions of from 94 to 98%, higher selectivities and substantially higher catalyst space velocities of from 0.44 to 0.45 kg of diethylene glycol per 1 of catalyst per h were achieved compared with the comparative catalyst A (cf. table 2, which shows, inter alia, the content of products in the reacted mixture in GC area % ([% by area]) and % by weight ([%])).

According to Table 2, selectivities for the two desired products of up to 69% (at 94% conversion of diethylene glycol) were achieved at about 200° C. at atmospheric pressure and with space velocities of about 0.44 kg of diethylene glycol per 1 of catalyst per h (catalyst G).

This constitutes an enormous improvement compared with catalyst A, which gave only 57% of desired product at a catalyst space velocity of 0.25 kg per 1 of catalyst per h and at a diethylene glycol conversion of 95%. The catalyst G, having a higher copper content than catalyst D, exhibited slightly higher activity.

TABLE 2

| Catalyst | Temp. [°C.] | Space velocity [kg/1$_{cat}$ * h] | Conversion diglycol [%] | BDMAE [%] | Selectivity DMEE [%] | Total [%] | Disp. % by area | Glycol cl. | LB |
|---|---|---|---|---|---|---|---|---|---|
| Cat. A | 200 | 0.2544 | 98.1 | 14.5 | 42.7 | 57.2 | 6.55 | 4.08 | 10.59 |
| Cat. B | 205 | 0.4544 | 97.2 | 17.1 | 44.4 | 61.5 | 6.98 | 2.61 | 8.18 |
| Cat. C | 200 | 0.4362 | 94.3 | 11.9 | 57.0 | 68.9 | 4.71 | 1.57 | 5.96 |

Abbreviations used:
BDMAE = bis(2-dimethylaminoethyl) ether
DMEE = 2-(2-dimethylaminoethoxy)ethanol
Disp. = sum of the products N-methylmorpholine and (N,N,N-trimethylbisamino)diethyl ether (in GC % by area) as a measure of the degree of disproportionation in the reaction
Glycol cl. = sum of the products N,N,N,N-tetramethyldiaminoethane and dimethylaminoethanol (in GC % by area) as a measure of the glycol cleavage of the starting material
LB = low boilers (= in GC, shorter retention time than DMEE)
¹cat. = bulk volume of the catalyst

EXAMPLE 3

Amination of diethylene glycol with dimethylamine

An experimental series for the synthesis of 2-(2-dimethylaminoethoxy)ethanol and bis(2-dimethylaminoethyl) ether from diethylene glycol and dimethylamine over comparative catalyst A and over catalyst D was carried out in apparatus 2.

The results obtained are shown in the table below (no. 3):

|  | Catalyst A (comparison) | Catalyst D |
|---|---|---|
| p [bar] | 20 | 20 |
| T [° C.] | 190 | 190 |
| H$_2$ feed [l (S.T.P.)/h] | 30 | 30 |
| Recycled gas [l (S.T.P./h] | 850 | 850 |
| DMA feed [g/h] | 10.8 | 10.8 |
| DEG feed [g/h] | 17.0 | 17.0 |
| whsv [kg/l·h] | 0.17 | 0.17 |
| MR (DMA/DEG)[c] | 1.5 | 1.5 |
| DEG [% by area][1] | 7.3 | 5.5 |
| DMEE [% by area][2] | 38.9 | 46.9 |
| BDMAE [% by area][3] | 25.3 | 24.8 |
| 'Σ [% by area]' | 'Σ64.2' | 'Σ71.7' |
| • byproducts |  |  |
| NMM [% by area][4] | 9.5 | 6.3 |
| Tri [% by area][5] | 0.47 | 0.44 |
| MEG [% by area][6] | <0.01 | <0.01 |
| DMEA [% by area][7] | 2.3 | 2.4 |
| TMEDA [% by area][8] | 0.87 | 0.46 |
| TEG [% by area][9] | <0.01 | <0.01 |
| 1,4-Dioxane [% by area] | 0.21 | 0.08 |
| • Conversion[a] | 92.7% | 94.5% |
| • Selectivity[b] | 69.3% | 75.9% |

Explanations for table 3:
[1] Diethylene glycol
[2] 2-(2-Dimethylaminoethoxy)ethanol
[3] Bis (2-dimethylaminoethyl) ether
[4] N-Methylmorpholine
[5] 2-Dimethylamino-2'-methylaminodiethyl ether
[6] Monoethylene glycol
[7] Dimethylethanolamine
[8] Tetramethylethylenediamine
[9] Tetraethylene glycol
[a] Conversion = 100 − DEG
[b] Selectivity = ((DMEE + BDMAE)/conversion) • 100
[c] MR = Molar ratio The experimental data indicate the following important advantages in the case of catalyst D compared with comparative catalyst A:

higher activity
    higher conversion of DEG and hence lower residual content in the discharge higher selectivity
    higher content of the desired products DMEE and BDMAE
    lower content of undesired byproducts (NMM formation reduced by 34% compared with catalyst A).

EXAMPLE 4

Amination of N-methyldiethanolamine with dimethylamine

An experimental series for the synthesis of 2,2-dimethylaminoethylmethylaminoethanol and N,N,N',N'',N''-pentamethyldiethylenetriamine from N-methyldiethanolamine and dimethylamine over various catalysts was carried out in apparatus 2.

PMDETA         Water $+ 2H_2O$

The results obtained are shown in the table below (no. 4):

|  | Catalyst A (comparison) | Catalyst D |
|---|---|---|
| p [bar] | 20 | 20 |
| T [° C.] | 200 | 200 |
| H$_2$ feed [1(S.T.P.)/h] | 30 | 30 |
| Recycled gas | 980 | 980 |

EXAMPLE 5

Amination of acetone to give isopropylamine and diisopropylamine

Acetone was fed together with ammonia and hydrogen (for conditions, cf. table 3) via a preheater at the stated pressures and temperatures in a straight pass into the reactor. The reactor discharge was let down into a separator and analyzed by GC.

The results are summarized in table 5, which shows, inter alia, the content of the products in the reacted mixture in GC% by area ([% by area]).

TABLE 5

| Temp. [° C.] | Pressure [bar] | Acetone [g/h] | Space velocity [kg/l$_{cat}$ * h] | NH$_3$ [g/h] | H$_2$ [1 (S.T.P.)/h] | Acetone/ NH$_3$ mol/mol | Isopropyl- amine % by area | Acetone % by area | Diisopropyl- amine % by area | Total % by area |
|---|---|---|---|---|---|---|---|---|---|---|
| 130 | 10 | 9.5 | 0.190 | 14.5 | 10 | 5.2 | 20 | 15.6 | 64.3 | 99.9 |
| 210 | 25 | 19 | 0.380 | 29 | 20 | 5.2 | 62.6 | 5.4 | 30.5 | 98.5 |
| 210 | 20 | 30 | 0.600 | 61.6 | 30 | 7.0 | 53.1 | 8.6 | 36.7 | 98.4 |

Reactor length: 30 cm catalyst D
Reactor volume (empty): 120 ml
Catalyst volume: 50 ml
Pressure: 20 bar -continued

|  | Catalyst A (comparison) | Catalyst D |
|---|---|---|
| [1(S.T.P.)/h] |  |  |
| DMA feed [g/h] | 22.7 | 22.7 |
| MDEA feed [g/h] | 30.0 | 30.0 |
| whsv [kg/1.h] | 0.3 | 0.3 |
| MR (DMA/MDEA)[c] | 2.0 | 2.0 |
| MDEA [% by area][1] | 19.4 | 16.2 |
| 'Tri' [Fl.-%][2] | 36.0 | 42.9 |
| PMDETA [% by area][3] | 7.1 | 9.4 |
| 'Σ [% by area]' | 'Σ43.1' | 'Σ52.3' |
| • Byproducts |  |  |
| MPip [% by area][4] | 0.88 | 0.26 |
| DMPip [% by area][5] | 2.1 | 2.2 |
| TetraMDETA [% by area][6] | 0.27 | 0.39 |
| • Conversion[a] | 80.6% | 83.8% |
| • Selectivity[b] | 53.5% | 62.4% |

Explanations for table 4:
[1] N-Methyldiethanolamine
[2] 2 2-Dimethylaminoethylmethylaminoethanol
[3] N,N,N',N",N"-Pentamethyldiethylenetriamine
[4] Methylpiperazine
[5] Dimethylpiperazine
[6] Tetramethyldiethylenetriamine
[a] Conversion = 100 - MDEA
[b] Selectivity = (('Tri' + PMDETA)/conversion) • 100
[c] MR = Molar ratio The experimental data show the following important advantages of catalyst D compared with catalyst A:

higher activity
  higher conversion of MDEA and hence lower residual content in the discharge
higher selectivity
  higher content of the desired products 'Tri' and PMDETA
  lower content of undesired byproducts (MPip formation reduced by 70% compared with catalyst A).

Examples 1 to 5 and the results for the mechanical properties of the catalysts show that the catalysts used in the novel process on the one hand have high mechanical stability and hence a long life under the reaction conditions and on the other hand give the products in high space-time yields.

We claim:

1. A process for the preparation of amines by reacting primary or secondary alcohols, aldehydes or ketones with nitrogen compounds selected from the group consisting of ammonia and primary and secondary amines at elevated temperatures and superatmospheric pressures in the presence of hydrogen and of a catalyst containing copper and oxygen-containing compounds of titanium, wherein the catalyst is used in the form of moldings which have been prepared with the addition of metallic copper powder.

2. A process as claimed in claim 1, wherein from 2 to 40% by weight, based on the catalytically active material of the catalyst, of copper powder are added for molding the catalyst.

3. A process as claimed in claim 1, wherein the moldings are pellets or extrudates.

4. A process as claimed in claim 1, wherein the catalytically active material of the catalyst prior to its reduction with hydrogen contains
  from 20 to 83% by weight of oxygen-containing compounds of titanium, calculated as TiO$_2$,
  from 15 to 60% by weight of oxygen-containing compounds of copper, calculated as CuO, and
  from 2 to 29% by weight of metallic copper, which was added before the molding of the catalyst material.

5. A process as claimed in claim 1, wherein the copper surface area of the catalyst is from 0.5 to 7 m$^2$ per g of catalyst.

6. A process as claimed in claim 1, wherein a part of the oxygen-containing compound of titanium in the catalyst is replaced by oxygen-containing compounds of aluminum and/or of zirconium and/or of silicon.

7. A process as claimed in claim 1, wherein the reaction over the fixed catalyst bed in the gas phase is carried out at from 80 to 300° C. and from 0.1 to 10 MPa.

8. A process as claimed in claim 1, wherein the reaction over the fixed catalyst bed in the liquid phase is carried out at from 130 to 250° C. and from 5 to 25 MPa.

9. A process as claimed in claim 1 for the preparation of amines of the formula I (I)

where $R^1$ and $R^2$ are each hydrogen, $C_{1-20}$-alkyl, $C_{3-12}$-cycloalkyl, aryl, $C_{7-20}$-aralkyl or $C_{7-20}$-alkylaryl or together are $(CH_2)_j$-X-$(CH_2)_k$, $R^3$ and $R^4$ are each hydrogen, alkyl, cycloalkyl, hydroxyalkyl, aminoalkyl, alkanolaminoalkyl, alkoxyalkyl, dialkylaminoalkyl, alkylaminoalkyl, $R^5$-$(OCR^6R^7CR^8R^9)_n$-$(OCR^6R^7)$, aryl, hetaryl, aralkyl, hetarylalkyl, alkylaryl, alkylhetaryl or Y-$(CH_2)_m$-$NR^5$-$(CH_2)_q$ or together are $(CH_2)_l$-X-$(CH_2)_m$ or $R^2$ and $R^4$ together are $(CH_2)_l$-X-$(CH_2)_m$, $R^5$ and $R^{10}$ are each hydrogen, $C_{1-4}$-alkyl or $C_{7-40}$-alkylphenyl, $R^6$, $R^7$, $R^8$ and $R^9$ are each hydrogen, methyl or ethyl,

X is $CH_2$, $CHR^5$, oxygen or $NR^5$,

Y is $N(R^{10})_2$, hydroxyl, $C_{2-20}$-alkylaminoalkyl or $C_{3-20}$-dialkylaminoalkyl, n is an integer from 1 to 30 and j, k, l, m and q are each an integer from 1 to 4, by reacting primary or secondary alcohols of the formula II (II)

with nitrogen compounds of the formula III (III)

10. A process as claimed in claim 1 for the preparation of diamines of the formula IV (IV)

where

Z is a $C_{2-12}$-alkylene chain which is unsubstituted or monosubstituted to trisubstituted by $C_{1-20}$-alkyl, $C_{1-20}$-alkoxy and/or $C_{2-20}$-dialkylamino and may be interrupted once or twice by oxygen or $NR^5$ and $R^1$, $R^2$, $R^3$, $R^4$ and $R^5$ are as defined in claim 9, by reacting diols of the formula V (V)

with nitrogen compounds of the formula III (III)

11. A process as claimed in claim 1 for the preparation of amines of the formula I (I)

where $R^1$, $R^2$, $R^3$ and $R^4$ have the meanings stated in claim 9, by reacting aldehydes or ketones of the formula VI and VII, respectively, (VI)

(VII)

with nitrogen compounds of the formula III (III)

* * * * *